United States Patent
Ahn et al.

(10) Patent No.: US 11,086,513 B2
(45) Date of Patent: Aug. 10, 2021

(54) METHOD AND APPARATUS FOR DISPLAYING FUNCTION OF BUTTON OF ULTRASOUND APPARATUS ON THE BUTTON

(71) Applicant: Samsung Electronics Co., Ltd., Suwon-si (KR)

(72) Inventors: Chi-young Ahn, Seoul (KR); Jong-chan Kwon, Yongin-si (KR); Ki-soo Kim, Gunpo-si (KR); Jung-hoon Kim, Seoul (KR); Sang-min Hyun, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 22 days.

(21) Appl. No.: 16/025,381

(22) Filed: Jul. 2, 2018

(65) Prior Publication Data

US 2018/0307409 A1    Oct. 25, 2018

Related U.S. Application Data

(63) Continuation of application No. 13/665,017, filed on Oct. 31, 2012, now Pat. No. 10,031,666.

(30) Foreign Application Priority Data

Apr. 26, 2012  (KR) .................. 10-2012-0043890

(51) Int. Cl.
*G06F 3/048* (2013.01)
*G06F 3/0488* (2013.01)
(Continued)

(52) U.S. Cl.
CPC .......... *G06F 3/04886* (2013.01); *A61B 8/467* (2013.01); *A61B 8/461* (2013.01); *G01S 7/52084* (2013.01)

(58) Field of Classification Search
CPC .. G06F 3/0482; G06F 3/0488; G06F 3/04815; G06F 3/0362; G06F 1/1626;
(Continued)

(56) References Cited

U.S. PATENT DOCUMENTS 5,715,823 A   2/1998  Wood et al.
7,904,824 B2  3/2011  Stern et al.
(Continued)

FOREIGN PATENT DOCUMENTS

CN   1716171 A    1/2006
CN   101098424 A  1/2009
(Continued)

OTHER PUBLICATIONS

Office Action dated Feb. 26, 2014, in U.S. Appl. No. 13/665,017.
(Continued)

*Primary Examiner* — Di Xiao
(74) *Attorney, Agent, or Firm* — Staas & Halsey LLP (57) ABSTRACT

A method of displaying a function of a button of an ultrasound apparatus on the button includes displaying information about one or more functions provided by the ultrasound apparatus, selecting one from among the one or more functions which have been displayed, determining a button in which the selected function is to be set based on an external input signal for matching the selected function to the button in which the selected function is to be set; and displaying information about the selected function on the determined button.

16 Claims, 7 Drawing Sheets

(51) Int. Cl.
*A61B 8/00* (2006.01)
*G01S 7/52* (2006.01)

(58) Field of Classification Search
CPC .. G06F 3/0481; G06F 3/04883; G06F 3/0346;
G06F 3/04886; G06F 1/169; G06F
2203/04802; G06F 3/038; G06F 1/1616;
G06F 1/1643; G06F 1/1647; G06F
1/1684; G06F 2200/1614; G06F
2200/1637; G06F 3/0236; G06F 3/0354;
G06F 3/03547; G06F 3/04817; G06F
3/0485; G06F 19/3406; G06F 1/1632;
G06F 1/1656; G06F 1/1677; G06F
1/1694; G06F 2203/0384; G06F
2203/04803; G06F 3/017; G06F 3/0486;
G06F 1/1601; G06F 1/1613; G06F
1/1637; G06F 1/1686; G06F 1/1692;
G06F 1/1698; G06F 2203/0339; G06F
2203/04806; G06F 2203/04807; G06F
3/01; G06F 3/012; G06F 3/0202; G06F
3/0238; G06F 3/0338; G06F 3/03542;
G06F 3/03545; G06F 3/0383; G06F
3/041; G06F 3/0416; G06F 3/0425; G06F
3/048; G06F 3/04842; G06F 3/04845;
G06F 3/04847; G06F 3/04892; G06F
3/04895; G06F 9/4443; B23D 59/002;
B23D 59/003; B23D 59/00
See application file for complete search history.

(56) References Cited

U.S. PATENT DOCUMENTS

| | | | |
|---|---|---|---|
| 8,069,420 B2 | 11/2011 | Plummer | |
| 8,085,244 B2 | 12/2011 | Shows | |
| 8,272,387 B2 | 9/2012 | Essex et al. | |
| 8,723,808 B2* | 5/2014 | Kim | G06F 3/04886 345/173 |
| 8,784,314 B2 | 7/2014 | Mathew | |
| 9,165,112 B2 | 10/2015 | Doyle | |
| 2004/0242988 A1 | 12/2004 | Niwa et al. | |
| 2005/0080326 A1 | 4/2005 | Mathew | |
| 2005/0131856 A1 | 6/2005 | O'Dea | |
| 2006/0020206 A1 | 1/2006 | Serra et al. | |
| 2006/0050142 A1 | 3/2006 | Scott et al. | |
| 2006/0058654 A1 | 3/2006 | Di Marco | |
| 2006/0068834 A1 | 3/2006 | Jones | |
| 2008/0079696 A1 | 4/2008 | Shim et al. | |
| 2008/0119731 A1 | 5/2008 | Becerra et al. | |
| 2008/0125655 A1 | 5/2008 | Song et al. | |
| 2009/0012394 A1 | 1/2009 | Hobelsberger | |
| 2009/0027347 A1 | 1/2009 | Wakefield et al. | |
| 2009/0043195 A1 | 2/2009 | Poland | |
| 2009/0131793 A1 | 5/2009 | Stonefield et al. | |
| 2009/0156934 A1 | 6/2009 | Lee et al. | |
| 2009/0164896 A1 | 6/2009 | Thorn | |
| 2009/0247874 A1 | 10/2009 | Kim | |
| 2010/0049050 A1 | 2/2010 | Pelissier | |
| 2010/0049051 A1 | 2/2010 | Sang et al. | |
| 2010/0094132 A1 | 4/2010 | Hansen et al. | |
| 2010/0145195 A1 | 6/2010 | Hyun | |
| 2010/0156865 A1* | 6/2010 | Kreek | G06F 1/1626 345/207 |
| 2010/0180219 A1 | 7/2010 | Sung et al. | |
| 2010/0191120 A1 | 7/2010 | Kraus et al. | |
| 2010/0251176 A1* | 9/2010 | Fong | G06F 3/04886 715/821 |
| 2010/0313029 A1 | 12/2010 | Abeln | |
| 2010/0321324 A1* | 12/2010 | Fukai | A61B 8/00 345/173 |
| 2010/0333044 A1* | 12/2010 | Kethireddy | G06F 3/0481 715/863 |
| 2011/0009169 A1* | 1/2011 | Kim | G06F 1/1692 455/566 |
| 2011/0058063 A1 | 3/2011 | Lee | |
| 2011/0190034 A1* | 8/2011 | Shin | G06F 3/041 455/566 |
| 2012/0069010 A1 | 3/2012 | Tian et al. | |
| 2012/0139845 A1 | 6/2012 | Griffin | |
| 2012/0145783 A1 | 6/2012 | Landau | |
| 2012/0172726 A1 | 7/2012 | Sakai | |
| 2012/0293431 A1 | 11/2012 | Hauf | |
| 2013/0018263 A1 | 1/2013 | Kimoto | |
| 2013/0035139 A1 | 2/2013 | Sheynblat et al. | |
| 2013/0137987 A1 | 5/2013 | Abe et al. | |
| 2013/0158397 A1 | 6/2013 | K. | |
| 2013/0165784 A1 | 6/2013 | Kim | |
| 2013/0194891 A1 | 8/2013 | Kristoffersen et al. | |
| 2013/0205206 A1* | 8/2013 | Hawver | G06F 9/485 715/704 |
| 2013/0219317 A1 | 8/2013 | Jo et al. | |
| 2013/0225999 A1 | 8/2013 | Banjanin | |
| 2013/0281855 A1 | 10/2013 | Baba et al. | |
| 2014/0005550 A1 | 1/2014 | Lu et al. | |
| 2014/0063219 A1 | 3/2014 | Stonefield | |
| 2014/0221835 A1 | 8/2014 | Ota | |
| 2014/0282142 A1 | 9/2014 | Lin | |
| 2014/0378833 A1 | 12/2014 | Cheng | |
| 2015/0002490 A1 | 1/2015 | Han et al. | |

FOREIGN PATENT DOCUMENTS

| | | |
|---|---|---|
| CN | 101595648 A | 12/2009 |
| CN | 101828380 A | 9/2010 |
| EP | 1 780 991 A1 | 5/2007 |
| EP | 1 925 257 A1 | 5/2008 |
| EP | 2458472 A1 | 5/2012 |
| JP | 2005-144154 | 6/2005 |
| JP | 2005-270317 | 10/2005 |
| JP | 2007-97816 | 4/2007 |
| JP | 2009-148 | 1/2009 |
| KR | 10-2009-0050423 | 5/2009 |
| KR | 10-2009-0076994 | 7/2009 |
| KR | 10-2010-0084037 | 7/2010 |
| KR | 10-2011-0089032 | 8/2011 |
| KR | 10-2011-0136098 | 12/2011 |
| WO | 2011/159034 A2 | 12/2011 |

OTHER PUBLICATIONS

Office Action dated Jun. 20, 2014, in U.S. Appl. No. 13/665,017.
Advisory Action dated Oct. 20, 2014, in U.S. Appl. No. 13/665,017.
Office Action dated Dec. 22, 2014, in U.S. Appl. No. 13/665,017.
Office Action dated Apr. 22, 2015, in U.S. Appl. No. 13/665,017.
Advisory Action dated Jul. 9, 2015, in U.S. Appl. No. 13/665,017.
Chinese Office Action dated Aug. 14, 2015 in corresponding Chinese Patent Application 201310149414.6.
Office Action dated Jun. 15, 2016, in U.S. Appl. No. 13/665,017.
Chinese Office Action dated Apr. 11, 2016 in corresponding Chinese Patent Application 201310149414.6.
Office Action dated Nov. 16, 2016, in U.S. Appl. No. 13/665,017.
Office Action dated Jun. 2, 2017, in U.S. Appl. No. 13/665,017.
Office Action dated Dec. 13, 2017, in U.S. Appl. No. 13/665,017.
Notice of Allowance dated Apr. 12, 2018, in U.S. Appl. No. 13/665,017.
Korean Office Action dated Mar. 19, 2018, in corresponding Korean Patent Application No. 10-2012-0043890.
U.S. Appl. No. 13/665,017, filed Oct. 31, 2012, Chi-young Ahn et al., Samsung Electronics Co., Ltd.
Korean Office Action dated Dec. 11, 2018 in Korean Patent Application No. 10-2018-0148774.

* cited by examiner

METHOD AND APPARATUS FOR DISPLAYING FUNCTION OF BUTTON OF ULTRASOUND APPARATUS ON THE BUTTON

CROSS-REFERENCE TO RELATED APPLICATIONS

This application is a continuation of U.S. application Ser. No. 13/665,017 filed Oct. 31, 2012, which claims the benefit of Korean Patent Application No. 10-2012-0043890, filed on Apr. 26, 2012, in the Korean Intellectual Property Office, the disclosure of which is incorporated herein in its entirety by reference.

BACKGROUND

1. Field

One or more embodiments of the present disclosure relate to a method and apparatus for displaying a function of a button of an ultrasound apparatus on the button, and more particularly, to a method and apparatus for setting a function of a button of an ultrasound apparatus based on an external input signal and displaying the set function on the button.

2. Description of the Related Art

Because they have non-invasive and non-destructive characteristics, ultrasound systems are widely used in medical applications for obtaining information about interior portions of a subject. Since ultrasound systems are capable of providing surgeons with real time high-resolution images of internal tissue of a human body without requiring surgery involving an incision, ultrasound systems are often very desirable for certain medical applications.

Ultrasound diagnostic apparatuses transmit an ultrasound signal to a predetermined portion in a subject's body from a surface of the body and obtain an image related to a section of soft tissue or a blood vessel by using information of the ultrasound signal reflected from the predetermined portion in the body.

Ultrasound diagnostic apparatuses have advantages such as small size, low cost, and capacity for real-time display. Also, since ultrasound diagnostic apparatuses have high stability without the risks inherent to X-ray radiation, ultrasound diagnostic apparatuses are widely used along with other diagnostic imaging apparatuses such as X-ray diagnostic apparatuses, computerized tomography (CAT) scanners, magnetic resonance imaging (MRI) apparatuses, and nuclear medicine diagnostic apparatuses. Also, because ultrasound systems may provide a high-resolution image visualizing an inner structure of a subject to surgeons in real time without requiring surgery involving an incision, ultrasound systems are very effectively used in medical applications.

SUMMARY

One or more embodiments of the present disclosure provide a method and apparatus for displaying a function of a button of an ultrasound apparatus on the button.

According to an aspect of the present disclosure, there is provided a method of displaying a function of a button of an ultrasound apparatus on the button, the method including: displaying information about one or more functions provided by the ultrasound apparatus; selecting one from among the one or more functions which have been displayed based on an external input signal; determining a button in which the selected function is to be set based on an external input signal for matching the selected function to the button in which the selected function is to be set; and displaying information about the selected function on the determined button.

The one or more functions may include a function of controlling an operation of the ultrasound apparatus.

The information about the function may include at least one of letters, numbers, symbols, and images, wherein the at least one of the letters, numbers, symbols, and images is editable based on an external input signal.

The displaying of the information may include displaying the information about the selected function on a display unit of the button.

The ultrasound apparatus may include at least one button, wherein the at least one button is disposed on a panel that is rotatable.

The method may further include: when the panel rotates, obtaining rotation information of the panel; and rotating the information about the selected function based on the rotation information and displaying the rotated information about the selected function on the determined button.

The rotation information may include a rotation direction and a rotation angle of the panel.

The rotating and displaying of the information may include rotating the information about the selected function in a direction opposite to the rotation direction of the panel by the rotation angle of the panel and displaying the rotated information.

The determining of the button may include: generating a virtual button; displaying the virtual button; and determining the virtual button in which the selected function is to be set based on an external input signal for matching the selected function to the virtual button in which the selected function is to be set.

The displaying of the information may include displaying the information about the selected function on the determined virtual button.

The method may further include: measuring an illumination in the area around the ultrasound apparatus; and changing a lightness based on the measured illumination and displaying the information about the selected function on the determined button at the changed lightness.

According to another aspect of the present disclosure, there is provided an apparatus for displaying a function of a button of an ultrasound apparatus on the button, the apparatus including: a user interface unit that displays information about one or more functions provided by the ultrasound apparatus; a selecting unit that selects one from among the one or more functions which have been displayed based on an external input signal; a determining unit that determines a button in which the selected function is to be set based on an external input signal for matching the selected button to the button in which the selected function is to be set; and a control unit that controls information about the selected function to be displayed on the determined button.

The one or more functions may include a function of controlling an operation of the ultrasound apparatus.

The information about the function may include at least one of letters, numbers, symbols, and images, wherein the at least one of the letters, numbers, symbols, and images is editable based on an external input signal.

Each button may include a display unit that displays the information about the function.

The ultrasound apparatus may include at least one button, wherein the at least one button is disposed on a panel that is rotatable.

The apparatus may further include a rotation information obtaining unit that, when the panel rotates, obtains rotation information of the panel, wherein the control unit controls the display unit to rotate the information about the selected function on the determined button based on the rotation information and display the rotated information.

The rotation information may include a rotation direction and a rotation angle of the panel, wherein the control unit controls the display unit to rotate the information about the selected function in a direction opposite to the rotation direction of the panel by the rotation angle of the panel and display the rotated information about the selected function.

The determining unit may include a virtual button generating unit that generates a virtual button.

The user interface unit may display the virtual button, and the determining unit may determine the virtual button in which the selected function is to be set based on an external input signal for matching the selected function to the virtual button in which the selected function is to be set.

The control unit may control the user interface unit to display the information about the selected function on the virtual button.

The apparatus may further include an illumination measuring unit that measures an illumination in the area around the ultrasound apparatus. The control unit may control the display unit to change a lightness based on the measured illumination and display the information about the selected function on the determined button at the changed lightness.

According to another aspect of the present disclosure, there is provided a computer-readable recording medium having embodied thereon a program for executing the method.

According to another aspect of the present disclosure an apparatus for displaying a function of an ultrasound apparatus is disclosed. The apparatus for displaying the function includes a selection unit to select a function of a plurality of functions of the ultrasound apparatus based on an external input signal and a control unit to display information indicating the function selected by the selection receiving on a button of the ultrasound apparatus.

According to another aspect of the present disclosure a method for displaying a function of an ultrasound apparatus is disclosed. The method includes selecting a function of a plurality of functions of the ultrasound apparatus based on an external input signal and displaying information indicating the selected function on a button of the ultrasound apparatus.

Additional aspects and/or advantages will be set forth in part in the disclosure that follows and, in part, will be apparent from the disclosure, or may be learned by practice of the disclosure.

BRIEF DESCRIPTION OF THE DRAWINGS

The above and other features and advantages of the present disclosure will become more apparent by describing in detail exemplary embodiments thereof with reference to the attached drawings in which.

DETAILED DESCRIPTION

Expressions such as "at least one of," when preceding a list of elements, may be interpreted as modify or referring to the entire list of elements following the expression.

The present disclosure will now be described more fully with reference to the accompanying drawings, in which exemplary embodiments of the disclosure are shown.

The terms used in the present disclosure are selected from among common terms that are currently widely used in consideration of their function in the present disclosure. However, the terms may be changed according to an intention of one of ordinary skill in the art, a precedent used in the art or a legal precedent, or the advent of new technology. Also, in particular cases, the terms are discretionally selected by the applicant of the present disclosure, and the meaning of those terms will be described in detail in the corresponding part of the detailed description. Therefore, the terms used in the present disclosure are not merely designations of the terms, but the terms are defined based on the meaning of the terms and content throughout the present disclosure.

Throughout the present application, when a part "includes" an element, it is to be understood that the part additionally includes other elements rather than excluding other elements as long as there is no particular opposing recitation. Also, the terms such as " . . . unit", "module", and the like used in the present disclosure indicate an unit, which processes at least one function or motion, and the unit may be implemented by hardware or software, or by a combination of hardware and software.

The present disclosure will now be described more fully with reference to the accompanying drawings to enable one of ordinary skill in the art to make and use the present disclosure without any difficulty. The disclosure may, however, be embodied in many different forms and should not be construed as being limited to the embodiments set forth herein; rather, these embodiments are provided so that this disclosure will be thorough and complete, and will fully convey the concept of the disclosure to those of ordinary skill in the art. Also, parts in the drawings unrelated to the detailed description are omitted to ensure clarity of the present disclosure. Like reference numerals in the drawings denote like elements.

For better understanding, an apparatus according to an embodiment of the present disclosure will be first explained with reference to FIG. 7.

Figure 7:
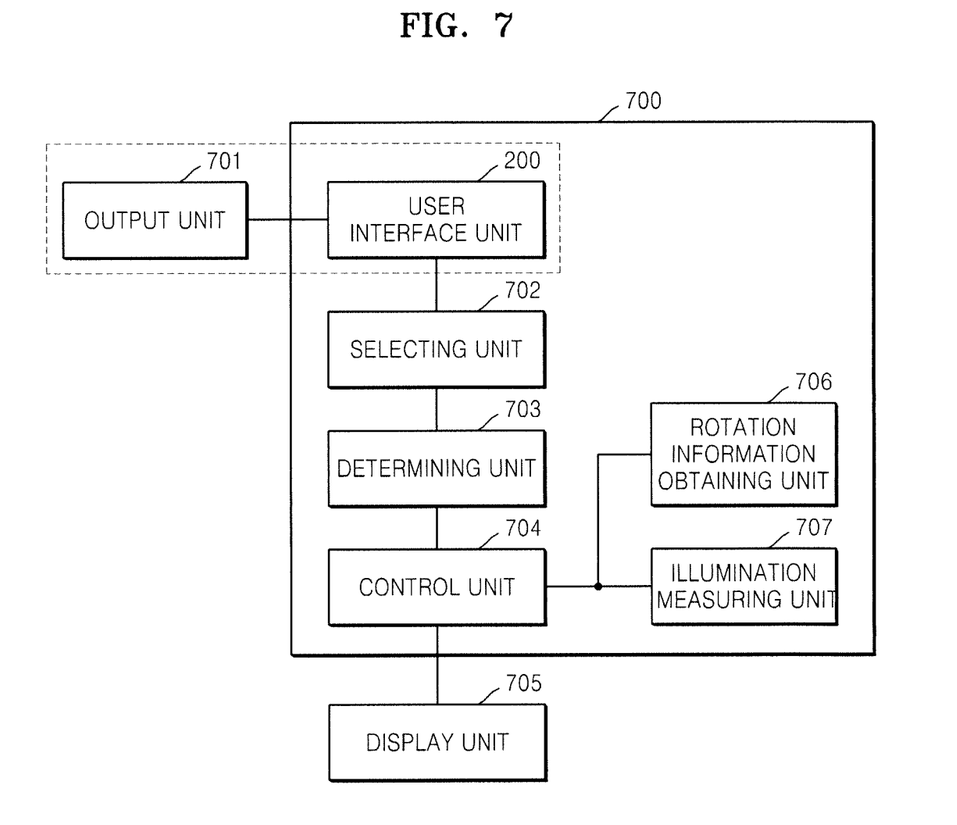
FIG. 7 is a block diagram illustrating an apparatus for displaying a function of a button of an ultrasound apparatus on the button, according to an embodiment of the present disclosure.

FIG. 7 is a block diagram illustrating an apparatus 700 for displaying a function of a button of an ultrasound apparatus on the button, according to an embodiment of the present disclosure.

Referring to FIG. 7, the apparatus 700 may include, for example, a user interface unit 200 that displays information about one or more functions provided by the ultrasound apparatus, a selecting unit 702 that selects one from the one or more functions, which have been displayed, based on an external input signal, a determining unit 703 that determines a button in which the selected function is to be set based on an external input signal for matching the selected function to the button in which the selected function is to be set, and a control unit 704 that controls information about the selected function to be displayed on the determined button.

The user interface unit 200 may be separate from an output unit 701 that includes a screen (not shown) on which an image of a subject is displayed. Alternatively, the user interface unit 200 may be included in the output unit 701.

The one or more functions may include a function of controlling an operation of the ultrasound apparatus.

Information about a function may include at least one of letters, numbers, symbols, and images, or any combination thereof. The at least one of the letters, numbers, symbols, and images may be edited based on an external input signal.

In FIG. 7, a button may include a display unit 705 that displays information about a function. The display unit 705 may be connected to the control unit 704.

Figure 3A:
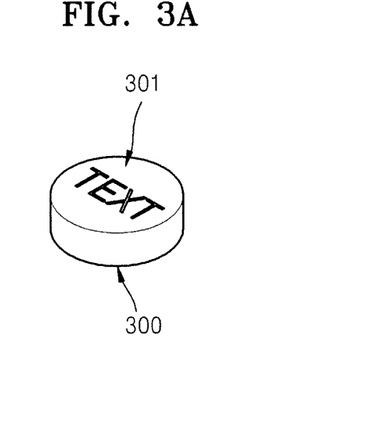
FIGS. 3A and 3B are perspective views illustrating a button of an ultrasound apparatus.
Figure 3B:
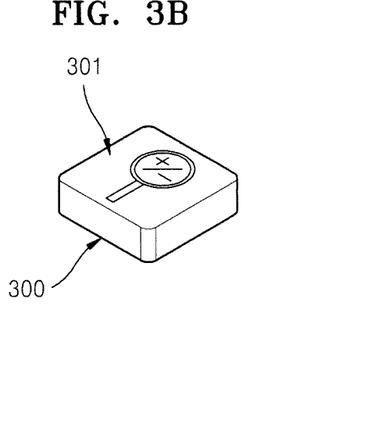

FIGS. 3A and 3B are perspective views illustrating a button 300 of the ultrasound apparatus, according to an embodiment of the present disclosure.

Figure 4:
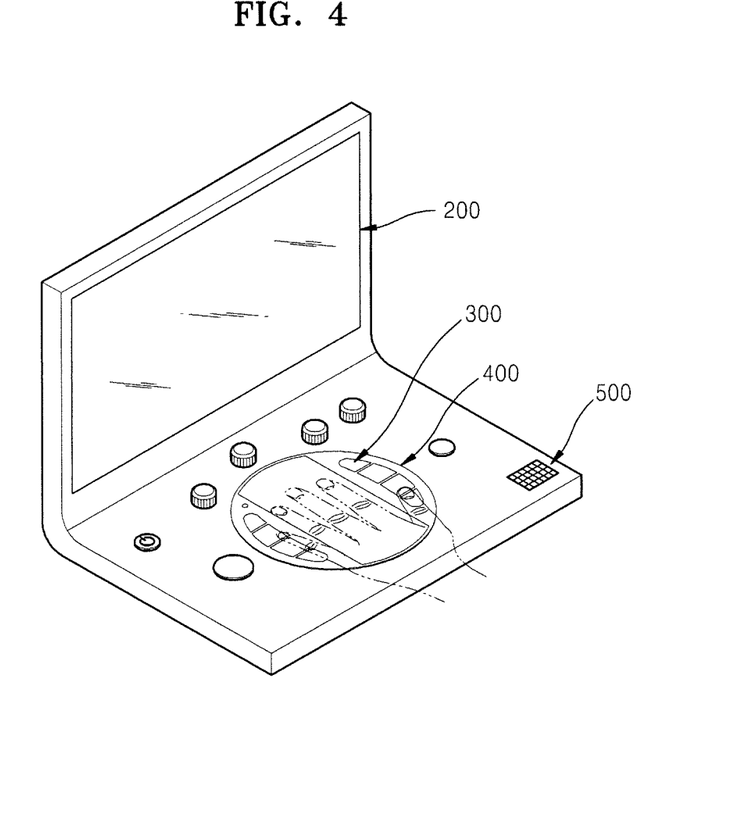
FIG. 4 is a perspective view illustrating an apparatus including a panel that is rotatable and includes at least one button, according to an embodiment of the present disclosure.

FIG. 4 is a perspective view illustrating an apparatus including a panel 400 that is rotatable and includes at least one button 300.

The ultrasound apparatus may include at least one button 300, and the button 300 may be located on the panel 400 that is rotatable.

The apparatus 700 may further include a rotation information obtaining unit 706 that, when the panel 400 rotates, obtains rotation information of the panel 400.

The control unit 704 may control the display unit 705 to rotate displayed information about the selected function on the determined button based on the rotation information and to display the rotated information about the selected function.

The rotation information may include at least one of a rotation direction and a rotation angle of the panel 400, and the control unit 704 may control the display unit 705 to rotate the displayed information about the selected function in a direction opposite to the rotation direction of the panel 400 based on the rotation angle of the panel 400 and to display the rotated information. For example, in an embodiment, if the panel is rotated clockwise ninety degrees, the control unit 704 may control the display unit 705 to rotate the displayed information counter-clockwise ninety degrees so that the display continues to reflect an orientation that facilitates the user's reading of the information displayed on the button. Other angles of rotation are equally possible.

Figure 6A:
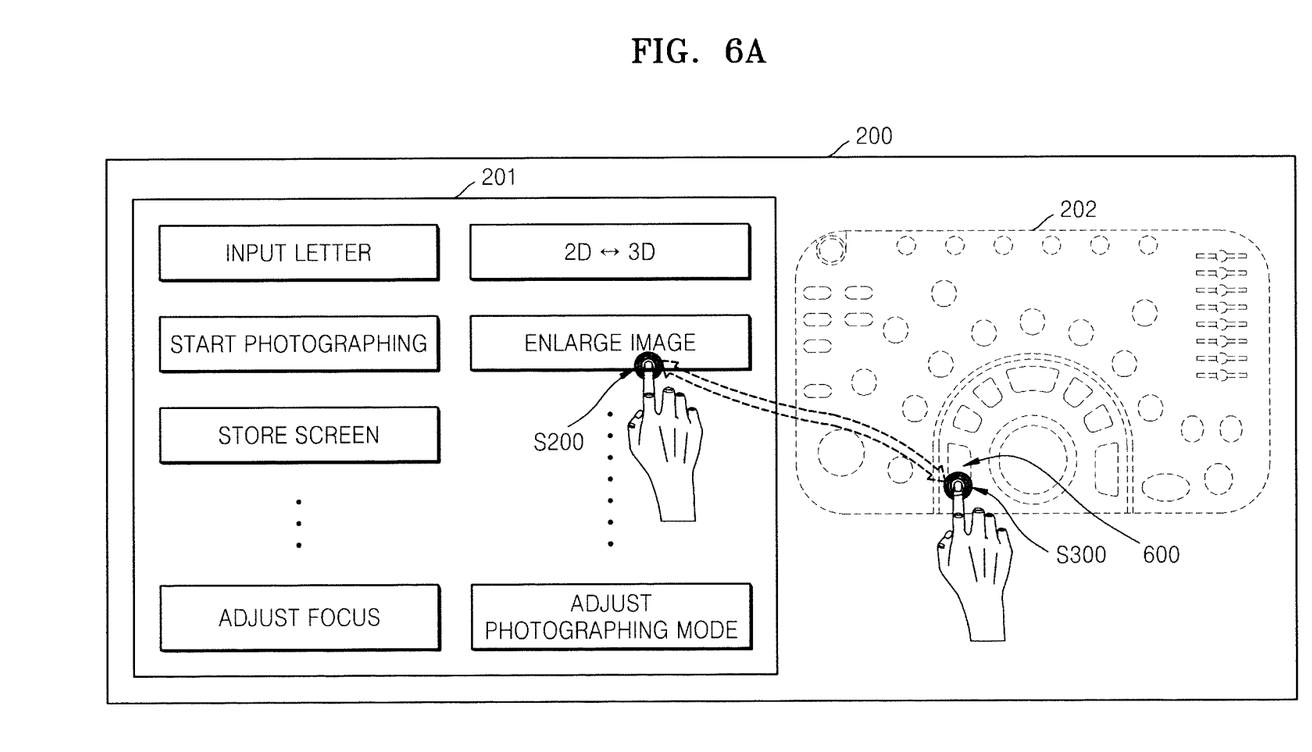
FIG. 6A is a view for explaining a process of selecting a function to be set in a virtual button and determining the virtual button in which the selected function is to be set.

FIG. 6A is a view for explaining a process of selecting a function to be set in a virtual button 600 and determining the virtual button 600 in which the selected function is to be set.

Figure 6B:
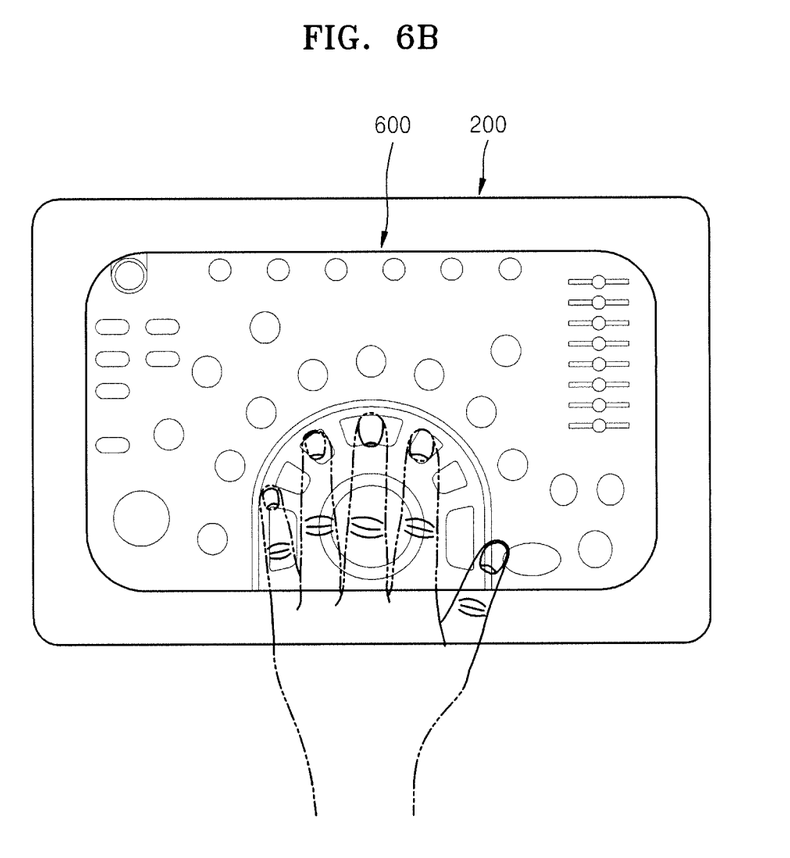
FIG. 6B is a view illustrating the virtual button in which the selected function is to be set.

FIG. 6B is a view illustrating the virtual button 600 in which the selected function is to be set.

Figure 8:
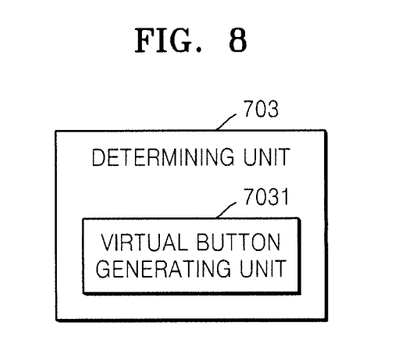
FIG. 8 is a block diagram illustrating a determining unit of the apparatus of FIG. 7.

FIG. 8 is a block diagram illustrating the determining unit 703 of the apparatus 700 of FIG. 7.

Referring to FIG. 8, the determining unit 703 may include a virtual button generating unit 7031 that generates the virtual button 600.

The user interface unit 200 may display the virtual button 600. For example, the user interface unit 200 may display both the virtual button 600 and the information about the one or more functions which have been displayed. In other words, as shown in FIG. 6A, the virtual button 600 and information 201 about one or more functions may be simultaneously displayed on the user interface unit 200.

The determining unit 703 may determine the virtual button 600 in which the selected function is to be set based on an external input signal for matching the selected function to the virtual button 600 in which the selected function is to be set. The external input signal may be based upon the user's selection of a particular function of the one or more displayed functions as further illustrated in 201 of FIG. 6A. Alternatively, the external input signal may be based upon an arbitrary selection of a particular function of the one or more displayed functions by the apparatus 700. In other words, each button may be arbitrarily set to correspond to a different function of the one or more functions without the need for display of the one or more functions and selection by a user.

The control unit 704 may control the user interface unit 200 to display the information about the selected function on the determined virtual button 600.

Also, the apparatus 700 may further include an illumination measuring unit 707 that measures an illumination in the area around the ultrasound apparatus. The control unit 704 may control the display unit 705 to change a lightness, e.g., an intensity, based on the measured illumination and to display the information about the selected function on the determined button at the changed lightness.

FIG. 4 is a perspective view illustrating the apparatus including the panel 400 that is rotatable and includes at least one button 300, according to an embodiment of the present disclosure.

The illumination measuring unit 707 may include an illumination sensor 500 that measures an illumination in the area around the ultrasound apparatus.

The description of the apparatus 700 may apply to the following method.

Figure 1:
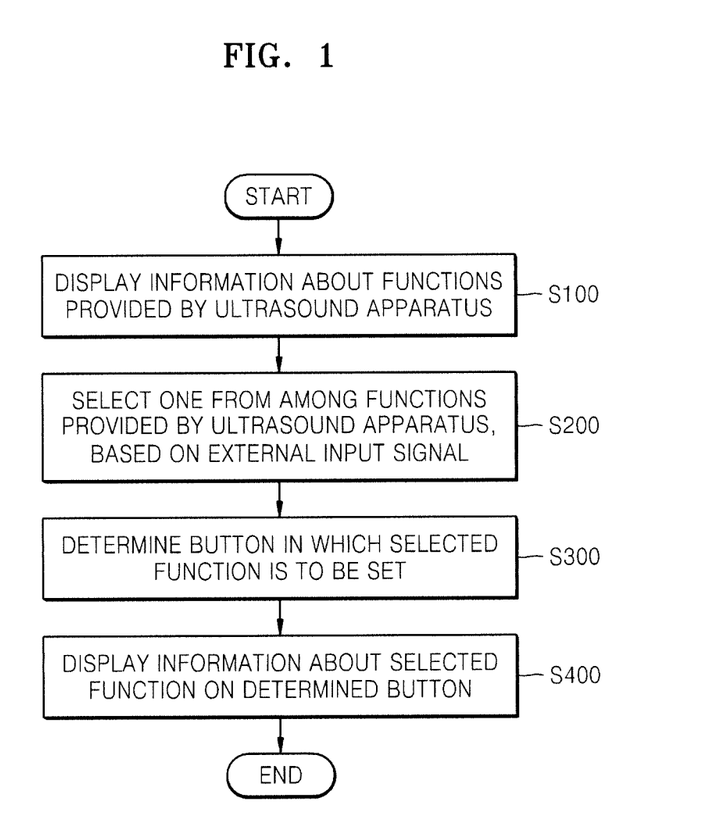
FIG. 1 is a flowchart illustrating a method of displaying a function of a button of an ultrasound apparatus on the button, according to an embodiment of the present disclosure.

FIG. 1 is a flowchart illustrating a method of displaying a function of a button of an ultrasound apparatus on the button, according to an embodiment of the present disclosure.

Referring to FIG. 1, the method may include operation S100 in which information about one or more functions provided by the ultrasound apparatus is displayed, operation S200 in which, based on an external input signal, one function is selected from among the one or more functions which have been displayed, operation S300 in which a button in which a selected function is to be set is determined based on an external input signal for matching the selected function to the button in which the selected function is to be set, and operation S400 in which information about the selected function is displayed on the determined button.

Also, the one or more functions may include a function of controlling an operation of the ultrasound apparatus.

For example, the one or more functions provided by the ultrasound apparatus may include a function of storing an image captured by using ultrasound waves, a function of inputting letters, numbers, symbols, and so on for the captured image, a function of selecting a predetermined portion from the captured image, a function of enlarging or reducing the captured image, a function of switching a photographing mode (for example, from a B mode to a color mode or from a 2D mode to a 3D mode), and a function of adjusting a focus on a subject, although any function capable of being performed by the ultrasound apparatus may be equally used.

Figure 2:
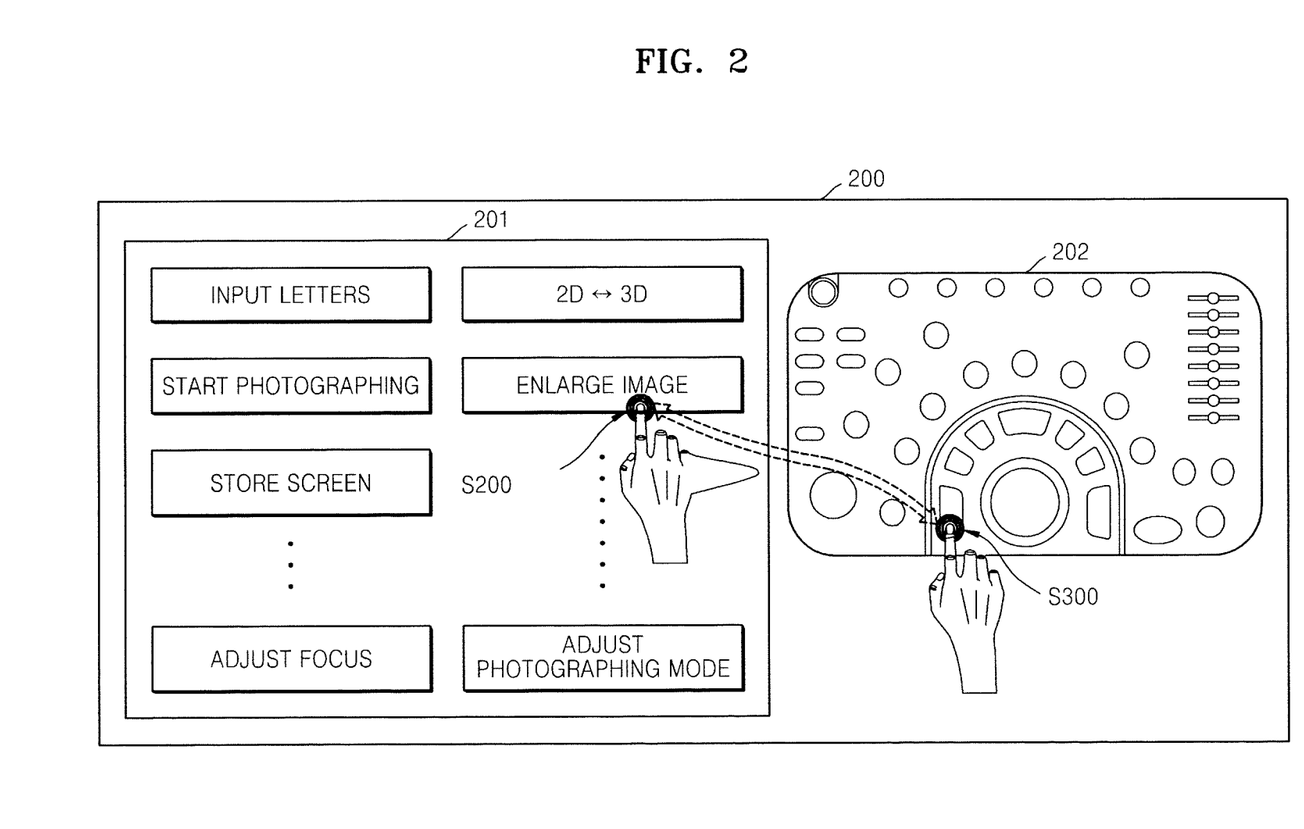
FIG. 2 is a view for explaining a process of selecting a function to be set in a button and determining the button in which the selected function is to be set.

FIG. 2 is a view for explaining a process of selecting a function to be set in a button, as in S200 for example, and determining the button in which the selected function is to be set, as in S300 for example.

Operation S100 in which the information about the one or more functions provided by the ultrasound apparatus is displayed may include displaying the information 201 about the one or more functions provided by the ultrasound apparatus on the user interface unit 200.

The information 201 about the one or more functions may include descriptions of the one or more functions. For example, the information 201 about the one or more functions may include at least one of letters, numbers, symbols, and images, although any information indicating the function may be equally used.

For example, the information 201 about the one or more functions provided by the ultrasound apparatus may be displayed in the form of letters (e.g., alphabet including consonants and vowels), numbers (e.g., Arabic numerals), or symbols (e.g., arrows). Alternatively, the information 201 about the one or more functions may be displayed in the form of images (e.g., icons).

The at least one of the letters, numbers, symbols, and images may be edited based on an external input signal. For example, the external input signal may include an input signal for performing enlargement, reduction, rotation, or display type change on the letters, numbers, symbols, or images by changing a plurality of pixel values of the letters, numbers, symbols, or images which have been displayed.

For example, as shown in FIG. 3A, when information about a function of inputting letters to an ultrasound image is displayed in the form of English letters 'TEXT', a display type of the information about the function may be changed by receiving an external input signal for editing the English letters 'TEXT' to Korean letters '문자 입력'. In this manner, the information about the function may be displayed in the form of various letters such as English letters, Chinese letters, Japanese letters, Russian letters, and French letters, although any letters from any other language may equally be used.

Alternatively, as shown in FIG. 3B, images may also be edited by changing pixel values in the same manner.

In other words, the letters, numbers, symbols, or images for indicating the information about the function may be changed by using bitmap editing or the like.

According to the present embodiment, the external input signal in operation S200 may include an external input signal for selecting any one from among pieces of information about the one or more functions which have been displayed. For example, the external input signal may include an input signal for the displayed pieces of information using a user's touch, a cursor, a direction key, or a numeric keypad.

Operation S300 in which the button in which the selected function is to be set is determined may include displaying button-related information 202 of the ultrasound apparatus.

As shown in FIG. 2, the button-related information 202 of the ultrasound apparatus may include an arrangement plan to arrange buttons.

Operation S300 in which the button is determined may include matching the selected function to the determined button.

The matching of the selected function to the determined button may include matching the information about the selected function 201 to the button-related information 202 of the ultrasound apparatus.

For example, the information 201 may be matched to the button-related information 202 by selecting any one from among the one or more functions which have been displayed and then determining a button to correspond to the selected one function by using the arrangement plan of the buttons which have been displayed. Alternatively, the information 201 may be matched to the button-related information 202 by determining a button by using the button-related information and then selecting any one from among the one or more functions which have been displayed. For example, the matching may be performed by dragging and dropping the information 201 about the selected function and the button-related information 202.

Also, the determining of the button may include determining the button according to an external input signal generated when a physical button of the ultrasound apparatus is pressed down without using the button-related information 202.

For example, the determining of the button may include, when any one is selected from among the one more functions which have been displayed, displaying at least one button in which the selected function is to be set, selecting any one from the at least one button which has been displayed, and matching the information 201 about the selected function to the button. The displaying of the at least one button in which the selected function is to be set may include blinking a backlight of a button in which the selected function is not yet set.

Furthermore, the method may determine a button in which a function is to be set, and then select the function to be set in the determined button. In other words, the method may include determining a button according to an external input signal generated when a physical button of the ultrasound apparatus is pressed down, selecting any one from among the one or more functions which have been displayed to be set in the determined button, and matching the determined button to the selected function. Alternatively, in another embodiment, the external input signal may be based upon an arbitrary selection of a particular function of the one or more displayed functions by the apparatus for displaying a function of a button of an ultrasound apparatus on the button. In other words, each button may be arbitrarily set to correspond to a different function of the one or more functions without needing to display the one or more functions and without needing selection of the functions by a user.

FIGS. 3A and 3B are perspective views illustrating the button 300 of the ultrasound apparatus.

Operation S400 in which the information about the selected function is displayed on the determined button may include displaying the information about the selected function on a display unit 301 of the button. The display unit 301 of the button may include a device such as a liquid crystal display (LCD) or an organic light-emitting diode (OLED) included in the button 300 although other types of display units may be equally used.

FIG. 4 is a perspective view illustrating the apparatus including the panel 400 that is rotatable and includes at least one button 300.

The ultrasound apparatus may include at least one button 300, and the at least one button 300 may be located on a rotatable panel 400. As the panel 400 rotates, the at least one button 300 included in the panel 400 may also rotate.

The method of displaying the function of the button of the ultrasound apparatus on the button may further include, when the panel 400 rotates, obtaining rotation information of the panel 400, rotating the information about the selected function based on the rotation information, and displaying the rotated information on the determined button.

Figure 5A:
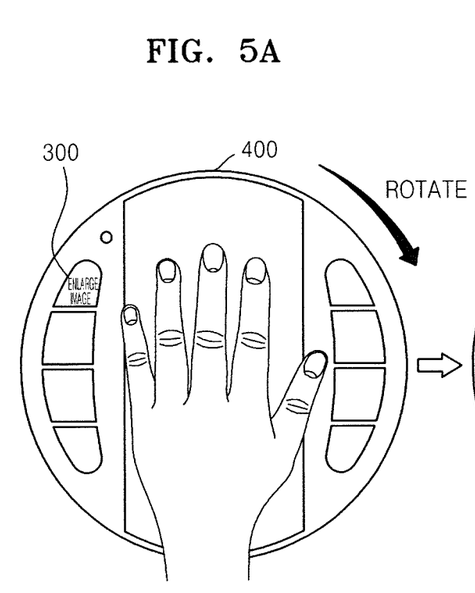
FIGS. 5A through 5C are views for explaining a process of, when the panel rotates, rotating information about a function set in a button and displaying the rotated information.
Figure 5B:
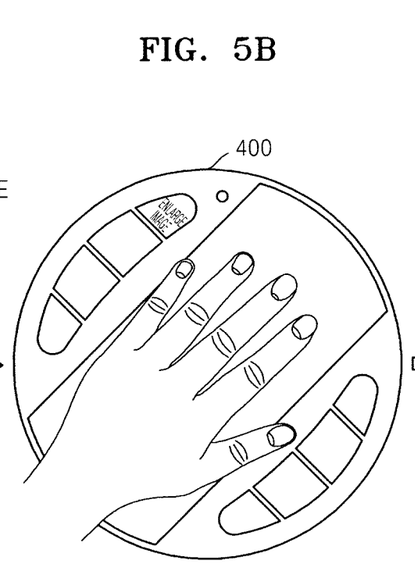
Figure 5C:
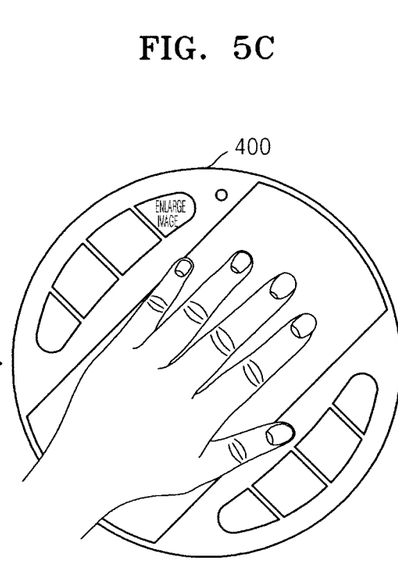

FIGS. 5A through 5C are views for explaining a process of, when the panel 400 rotates, rotating information about a function set in the button 300 and displaying the rotated information about the selected function.

The rotation information may include a rotation direction and a rotation angle of the panel 400. Also, the rotating and displaying of the information may include rotating the information about the selected function in a direction opposite to the rotation direction of the panel 400 by the rotation angle of the panel 400 and displaying the rotated information about the selected function. For example, in an embodiment, if the panel 400 is rotated clockwise ninety degrees, the information displayed on the button 300 may be rotated counter-clockwise ninety degrees so that the information displayed on the button 300 continues to reflect an orientation that facilitates the user's reading of the information displayed on the button 300. Other angles of rotation are equally possible.

Referring to FIGS. 5A and 5B, when the panel 400 rotates, information about the rotation direction and the rotation angle of the panel 400 may be obtained based on an amount by which the panel 400 rotates. Referring to FIG. 5B, as the panel 400 rotates, the button 300 included in the panel 400 is rotated, the information about the function set in the button 300 may be rotated by the amount by which the panel 400 rotates, and the rotated information may be displayed. As such, the information about the function set in the button 300 may be obliquely displayed as the panel 400 rotates, thereby degrading readability for the user. In other words, the information may be oriented at a right angle with respect to the user making it more difficult to read the information.

As shown in FIG. 5C, the information about the function set in the button 300 may be corrected and then displayed so that a direction in which the user views the button 300 is constant by rotating the information about the function set in the button 300 in a direction opposite to the rotation direction of the panel 400 by the amount by which the panel 400 rotates and displaying the rotated information. For example, the rotating and displaying of the information may include rotating the information about the function set in the button 300 in a direction opposite to the rotation direction of the panel 400 by the rotation angle of the panel 400 and displaying the rotated information.

FIG. 6A is a view for explaining a process of selecting a function to be set in a virtual button and determining the virtual button in which the selected function is to be set. FIG. 6B is a view illustrating the virtual button in which the selected function is to be set.

Operation S300 in which the button is determined may include generating the virtual button 600, displaying the virtual button 600, and determining the virtual button 6020 in which the selected function is to be set based on an external input signal for matching the selected function to the virtual button 600 in which the selected function is to be set.

A button of the ultrasound apparatus may be the virtual button 600. For example, a button of the ultrasound apparatus may include the virtual button 600 that is displayed on the user interface unit 200 instead of a button that protrudes from the ultrasound apparatus.

The virtual button 600 may be configured in a preset arrangement. For example, the virtual button 600 may be configured according to a preset arrangement. The arrangement of the virtual button 600 may be changed in various ways according to an external input signal.

The virtual button 600 may be displayed on the user interface unit 200.

The displaying of the virtual button 600 may further include displaying both the information 21 about the one or more functions which have been displayed and the virtual button 600. For example, as shown in FIG. 6A, the virtual button 600 and the information 201 about the one or more functions may be simultaneously displayed on the user interface unit 200.

The description of the matching of the information 201 about the selected function to the virtual button 600 has already been provided above.

Operation S400 in which the information is displayed may include displaying the information 201 about the selected function on the virtual button 600. As shown in FIG. 6B, the virtual button 600 in which each function is determined may be displayed on the user interface unit 200, and information about the function set in the virtual button may also be displayed on the displayed virtual button 600.

An operation of the ultrasound apparatus may be controlled by using the virtual button 600 in which a function is set. In other words, the virtual button 600 in which a function is set may be displayed on the user interface unit 200 as shown in FIG. 6B, and an operation of the ultrasound apparatus may be controlled by using the virtual button 600. Thus, by displaying information that describes the function of the virtual button 600 on the virtual button 600, a user may more easily select a button necessary to perform a function desired by the user.

The method may further include measuring an illumination in the area around the ultrasound apparatus, changing a lightness based on the measured illumination, and displaying the information about the selected function on the determined button at the changed lightness. For example, a lightness may be changed according to an illumination in the area around the ultrasound apparatus and information about a function set in a button may be displayed at the changed lightness.

The measuring of the illumination in the area around the ultrasound apparatus may include measuring the illumination in the area around the ultrasound apparatus by using, for example, illumination sensor 500.

For example, when the illumination in the area around the ultrasound apparatus is high, the information about the function set in the button may be displayed by gradually increasing the lightness of the information about the function set in the button, and when the illumination is low, the information about the function set in the button may be displayed by gradually reducing the lightness of the information about the function set in the button.

Meanwhile, the above-described embodiments of the present disclosure may be implemented as an executable program, and may be executed by a general-purpose digital computer that runs the program by using a non-transitory computer-readable recording medium.

Examples of the non-transitory computer-readable recording medium include magnetic media such as hard disks, floppy disks, and magnetic tape; optical media such as CD ROM disks and DVDs; magneto-optical media such as optical disks; and hardware devices that are specially configured to store and perform program instructions, such as read-only memory (ROM), random access memory (RAM), flash memory, and the like. Examples of program instructions include both machine code, such as produced by a compiler, and files containing higher level code that may be executed by the computer using an interpreter. The described hardware devices may be configured to act as one or more software modules in order to perform the operations of the above-described embodiments, or vice versa.

Any one or more of the software modules described herein may be executed by a controller such as a dedicated processor unique to that unit or by a processor common to one or more of the modules. The described methods may be executed on a general purpose computer or processor or may be executed on a particular machine such as the apparatus displaying a function of a button of an ultrasound apparatus on the button described herein.

While the present disclosure has been particularly shown and described with reference to exemplary embodiments thereof using specific terms, the embodiments and terms have been used to explain the present disclosure and should not be construed as limiting the scope of the present disclosure defined by the claims. The exemplary embodiments should be considered in a descriptive sense only and not for purposes of limitation. Therefore, the scope of the disclosure is defined not by the detailed description of the disclosure but by the appended claims, and all differences within the scope will be construed as being included in the present disclosure.

What is claimed is:

1. An ultrasound apparatus comprising:
    a touch screen control panel;
    at least one memory storing instructions; and
    at least one processor which executes the stored instructions to cause the following to be performed:
        displaying a plurality of virtual buttons on the touch screen control panel, each button of the plurality of virtual buttons displaying information thereon about a function of the ultrasound apparatus and being operable to cause the ultrasound apparatus to perform the function, wherein the information is displayed in the form of at least one of letters, numbers, symbols, and images,
        receiving, through the touch screen control panel, a touch input for selecting the information displayed on a virtual button from among the plurality of virtual buttons and a drag-and-drop input for moving a position of the selected information, and
        changing a size of the selected information by performing enlargement or reduction of the information based on the touch input and the drag-and-drop input, wherein
            the virtual button having the changed size information displayed thereon is operable by a touch input for selecting the virtual button through the touch screen control panel, and
            operation of the virtual button by the touch input for selecting the virtual button is not affected by the change in size of the information displayed on the virtual button.

2. The ultrasound apparatus of claim 1, wherein the at least one processor executes the stored instructions to further cause the following to be performed:
    displaying, by the touch screen control panel, labels describing functions, respectively, of the ultrasound apparatus.

3. The ultrasound apparatus of claim 2, wherein the at least one processor executes the stored instructions to further cause the following to be performed:
    selecting a first label describing a first function from among the functions, from among the displayed labels, in response to a single touch input through the touch screen control panel,
    determining a first virtual button from among the plurality of virtual buttons in which the selected label is to be set, in response to a drag-and-drop input through the touch screen control panel for matching the selected label to the first virtual button, and
    displaying the first label on the determined first virtual button as the information displayed on the first virtual button.

4. The ultrasound apparatus of claim 1, wherein the at least one processor executes the stored instructions to further cause the following to be performed:
    displaying a virtual trackball on the touch screen control panel.

5. The ultrasound apparatus of claim 2, wherein the labels comprise at least one of letters, numbers, symbols, and images.

6. The ultrasound apparatus of claim 1, wherein
    the virtual button is rotatable, and
    the at least one processor executes the stored instructions to further cause the following to be performed:
        obtaining rotation information relating to the virtual button, and
        rotating the information displayed on the virtual button, relative to the virtual button, based on the obtained rotation information.

7. The ultrasound apparatus of claim 1, wherein
    the virtual button is rotatable, and
    the at least one processor executes the stored instructions to further cause the following to be performed:
        obtaining rotation information relating to rotation of the virtual button, the rotation information comprising at least one of a rotation direction of the virtual button and a rotation angle related to rotation of the virtual button, and
        rotating the information displayed on the virtual button in a direction opposite to the rotation direction according to the rotation angle.

8. The ultrasound apparatus of claim 1, wherein
    the at least one processor executes the stored instructions to further cause the following to be performed:
        measuring an illumination in the area around the ultrasound apparatus,
        changing an intensity based on the measured illumination, and displaying the information on the virtual button at the changed intensity.

9. A method for operating an ultrasound apparatus, the method comprising:
    displaying, on a touch screen display of the ultrasound apparatus that operates as a control panel of the ultrasound apparatus, a plurality of virtual buttons, each button of the plurality of virtual buttons displaying information thereon about a function of the ultrasound apparatus and being operable to cause the ultrasound apparatus to perform the function, wherein the information is displayed in the form of at least one of letters, numbers, symbols, and images;

receiving, by the touch screen display, a touch input for selecting the information displayed on a virtual button from among the plurality of virtual buttons and a drag-and-drop input for moving a position of the selected information; and changing a size of the selected information by performing enlargement or reduction of the information based on the touch input and the drag-and-drip input, wherein the virtual button having the changed size information displayed thereon is operable by a touch input for selecting a virtual button through the touch screen display, and operation of the virtual button by the touch input for selecting the virtual button is not affected by the change in size of the information displayed on the virtual button.

10. The method of claim 9, wherein the displaying of the plurality of virtual buttons comprises respectively displaying labels describing functions on the touch screen display.

11. The method of claim 10, further comprising:
selecting a first label describing a first function from among the functions, from among the displayed labels, in response to a single touch input through the touch screen display;
determining a first virtual button from among the plurality of virtual buttons in which the selected label is to be set, in response to a drag-and-drop input through the touch screen display for matching the selected label to the first virtual button; and
displaying the first label on the determined first virtual button as the information displayed on the first virtual button.

12. The method of claim 9, further comprising:
displaying a virtual trackball on the touch screen display.

13. The method of claim 9, wherein the virtual button is rotatable, and the method further comprises:
obtaining rotation information relating to the virtual button; and
rotating the information displayed on the virtual button, relative to the virtual button, based on the obtained rotation information.

14. The method of claim 9, wherein the virtual button is rotatable, and the method further comprises:
obtaining rotation information relating to rotation of the virtual button, the rotation information comprising at least one of a rotation direction of the virtual button and a rotation angle related to rotation of the virtual button; and
rotating the information displayed on the virtual button in a direction opposite to the rotation direction according to the rotation angle.

15. The method of claim 9, further comprises:
measuring an illumination in an area around the ultrasound apparatus;
changing an intensity based on the measured illumination; and
displaying the information on the virtual button at the changed intensity.

16. A non-transitory computer-readable storage medium storing a computer program for operating an ultrasound apparatus, wherein the program comprises instructions to perform:
displaying, on a touch screen display of the ultrasound apparatus that operates as a control panel of the ultrasound apparatus, a plurality of virtual buttons, each button of the plurality of virtual buttons displaying information thereon about a function of the ultrasound apparatus and being operable to cause the ultrasound apparatus to perform the function, wherein the information is displayed in the form of at least one of letters, numbers, symbols, and images;
receiving, by the touch screen display, a touch input for selecting the information displayed on a virtual button from among the plurality of virtual buttons and a drag-and-drop input for moving a position of the selected information; and
changing a size of the selected information by performing enlargement or reduction of the information based on the touch input and the drag-and-drop input, wherein
the virtual button having the changed size information displayed thereon is operable by a touch input for selecting a virtual button through the touch screen display, and
operation of the virtual button by the touch input for selecting the virtual button is not affected by the change in size of the information displayed on the virtual button.

* * * * *

UNITED STATES PATENT AND TRADEMARK OFFICE
CERTIFICATE OF CORRECTION

| | |
|---|---|
| PATENT NO. | : 11,086,513 B2 |
| APPLICATION NO. | : 16/025381 |
| DATED | : August 10, 2021 |
| INVENTOR(S) | : Chi-young Ahn et al. |

Page 1 of 1

It is certified that error appears in the above-identified patent and that said Letters Patent is hereby corrected as shown below:

In the Claims

Column 13, Line 10:
In Claim 9, delete "drag-and-drip" and insert --drag-and-drop--, therefor.

Signed and Sealed this
Twenty-fifth Day of October, 2022

*Katherine Kelly Vidal*
Katherine Kelly Vidal
*Director of the United States Patent and Trademark Office*